US006350280B1

(12) United States Patent
Nash et al.

(10) Patent No.: US 6,350,280 B1
(45) Date of Patent: Feb. 26, 2002

(54) SURGICAL CONNECTOR SYSTEMS AND METHODS OF USE

(75) Inventors: John E. Nash, Chester Springs; Douglas G. Evans, Downington; David M. Hoganson, West Chester, all of PA (US)

(73) Assignee: Kensey Nash Corporation, Exton, PA (US)

( * ) Notice: Subject to any disclaimer, the term of this patent is extended or adjusted under 35 U.S.C. 154(b) by 0 days.

(21) Appl. No.: 09/497,274

(22) Filed: Feb. 3, 2000

Related U.S. Application Data

(63) Continuation of application No. 08/923,682, filed on Sep. 4, 1997, now Pat. No. 6,063,114.

(51) Int. Cl.[7] .................................................. A61F 2/00
(52) U.S. Cl. ...................................... 623/1.36; 606/153
(58) Field of Search ................................ 623/1.1, 1.14, 623/1.36; 606/153, 151, 213

(56) References Cited

U.S. PATENT DOCUMENTS

| | | |
|---|---|---|
| 2,127,903 A | 8/1938 | Bowen |
| 3,155,095 A | 11/1964 | Brown |
| 3,588,902 A | 6/1971 | Wesolowski |
| 3,620,218 A | 11/1971 | Schmitt et al. |
| 3,683,926 A | 8/1972 | Suzuki |
| 4,214,586 A | 7/1980 | Mericle |
| 4,233,981 A | 11/1980 | Schomacher |
| 4,352,358 A | 10/1982 | Angelchik |
| 4,366,819 A | 1/1983 | Kaster |
| 4,368,736 A | 1/1983 | Kaster |
| 4,470,415 A | 9/1984 | Wozniak |
| 4,501,263 A | 2/1985 | Harbuck |
| 4,512,761 A | 4/1985 | Raible |
| 4,523,592 A | 6/1985 | Daniel |
| 4,552,148 A | 11/1985 | Hardy, Jr. et al. |
| 4,553,542 A | 11/1985 | Schenck et al. |
| 4,657,019 A | 4/1987 | Walsh et al. |
| 4,675,008 A | 6/1987 | Tretbar |
| 4,721,109 A | 1/1988 | Healey |
| 4,744,364 A | 5/1988 | Kensey |
| 4,753,236 A | 6/1988 | Healey |
| 4,769,029 A | 9/1988 | Patel |
| 4,816,028 A | 3/1989 | Kapadia et al. |
| 4,851,001 A | 7/1989 | Taheri |
| 4,852,568 A | 8/1989 | Kensey |
| 4,854,318 A | 8/1989 | Solem et al. |
| 4,930,502 A | 6/1990 | Chen |
| 4,931,057 A | 6/1990 | Cummings et al. |
| 4,957,499 A | 9/1990 | Lipatov et al. |
| 5,053,046 A | 10/1991 | Janese |

(List continued on next page.)

FOREIGN PATENT DOCUMENTS

| WO | WO 96/25886 | 8/1996 |
|---|---|---|
| WO | WO 97/40754 | 11/1997 |

*Primary Examiner*—Michael J. Milano
(74) *Attorney, Agent, or Firm*—Caesar, Rivise, Bernstein, Cohen & Pokotilow, Ltd.

(57) ABSTRACT

A system and method of use for effecting the bypass or other anastomosis of a portion of a native blood vessel, duct, lumen or other tubular organ within the body of a living being. The system includes a connector assembly and a deployment instrument for carrying the device to the desired position within the vessel, duct, lumen or tubular organ. The system includes a piercer-dilator instrument to form an opening in the wall of the vessel, duct, lumen or tubular organ into which the connector assembly is deployed by the deployment instrument. The connector assembly is at least partially formed of a resorbable material and includes movable members for securing it to the tissue of the vessel, duct, lumen or tubular organ contiguous with the opening. Other components may be included in the device for expediting the anastomosis procedure, with or without the use of sutures.

34 Claims, 6 Drawing Sheets

U.S. PATENT DOCUMENTS

| | | |
|---|---|---|
| 5,123,908 A | 6/1992 | Chen |
| 5,156,619 A | 10/1992 | Ehrenfeld |
| 5,192,289 A | 3/1993 | Jessen |
| 5,222,963 A | 6/1993 | Brinkerhoff et al. |
| 5,250,058 A | 10/1993 | Miller et al. |
| 5,304,195 A | 4/1994 | Twyford, Jr. et al. |
| 5,309,894 A | 5/1994 | Heckele et al. |
| 5,330,490 A | 7/1994 | Wilk et al. |
| 5,342,393 A | 8/1994 | Stack |
| 5,346,501 A | 9/1994 | Regula et al. |
| 5,364,389 A | 11/1994 | Anderson |
| RE34,866 E | 2/1995 | Kensey et al. |
| 5,397,331 A | 3/1995 | Himpens et al. |
| 5,399,352 A | 3/1995 | Hanson |
| 5,411,520 A | 5/1995 | Nash et al. |
| 5,417,691 A | 5/1995 | Hayhurst |
| 5,425,738 A | 6/1995 | Gustafson et al. |
| 5,425,739 A | 6/1995 | Jessen |
| 5,443,497 A | 8/1995 | Venbrux |
| 5,445,644 A | 8/1995 | Pietrafitta et al. |
| 5,447,514 A | 9/1995 | Gerry et al. |
| 5,456,712 A | 10/1995 | Maginot |
| 5,456,714 A | 10/1995 | Owen |
| 5,503,635 A | 4/1996 | Sauer et al. |
| 5,509,902 A | 4/1996 | Raulerson |
| 5,545,178 A | 8/1996 | Kensey et al. |
| 5,549,617 A | 8/1996 | Green et al. |
| 5,571,167 A | 11/1996 | Maginot |
| 5,586,987 A | 12/1996 | Fahy |
| 5,591,226 A | 1/1997 | Trerotola et al. |
| 5,601,557 A | 2/1997 | Hayhurst |
| 5,649,959 A | 7/1997 | Hannam |
| 5,676,670 A | 10/1997 | Kim |
| 5,695,504 A | 12/1997 | Gifford, III et al. |
| 5,709,335 A | 1/1998 | Heck |
| 5,766,220 A | 6/1998 | Moenning |
| 5,797,934 A | 8/1998 | Rygaard |

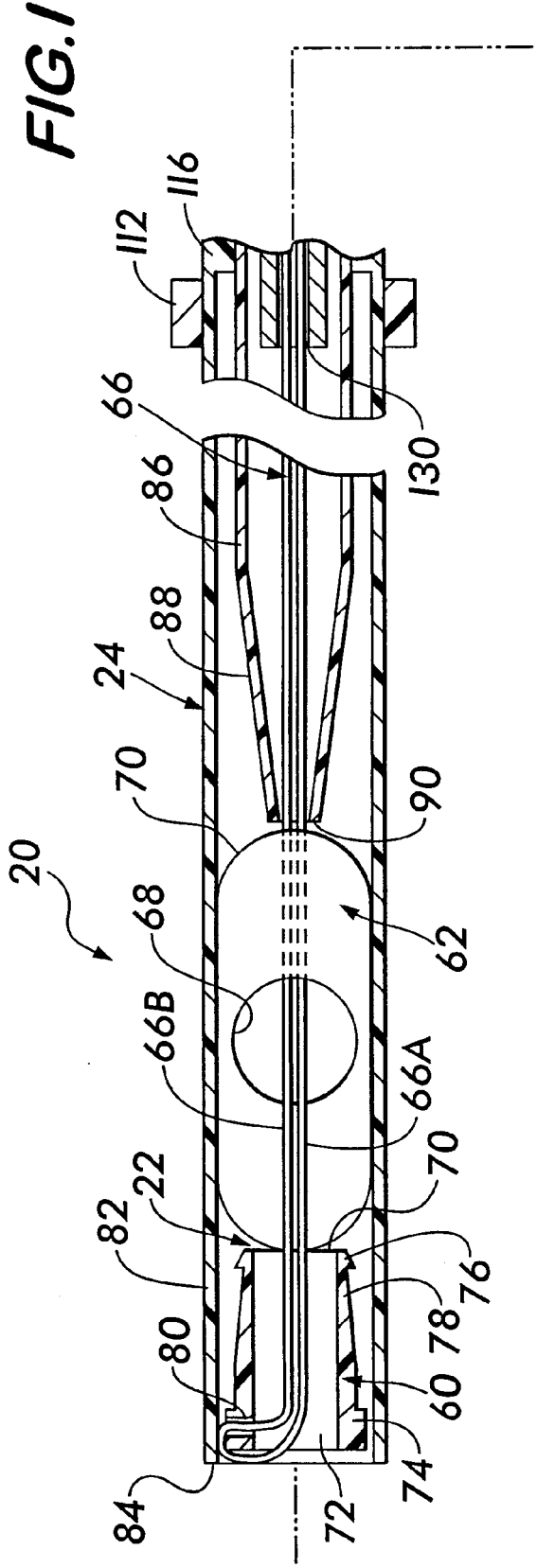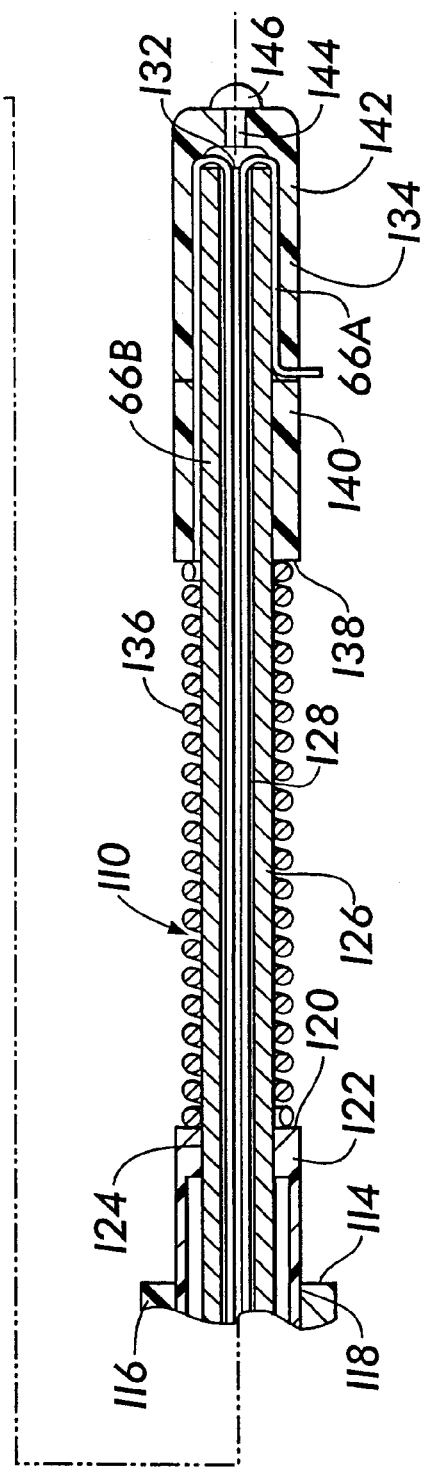
FIG.1

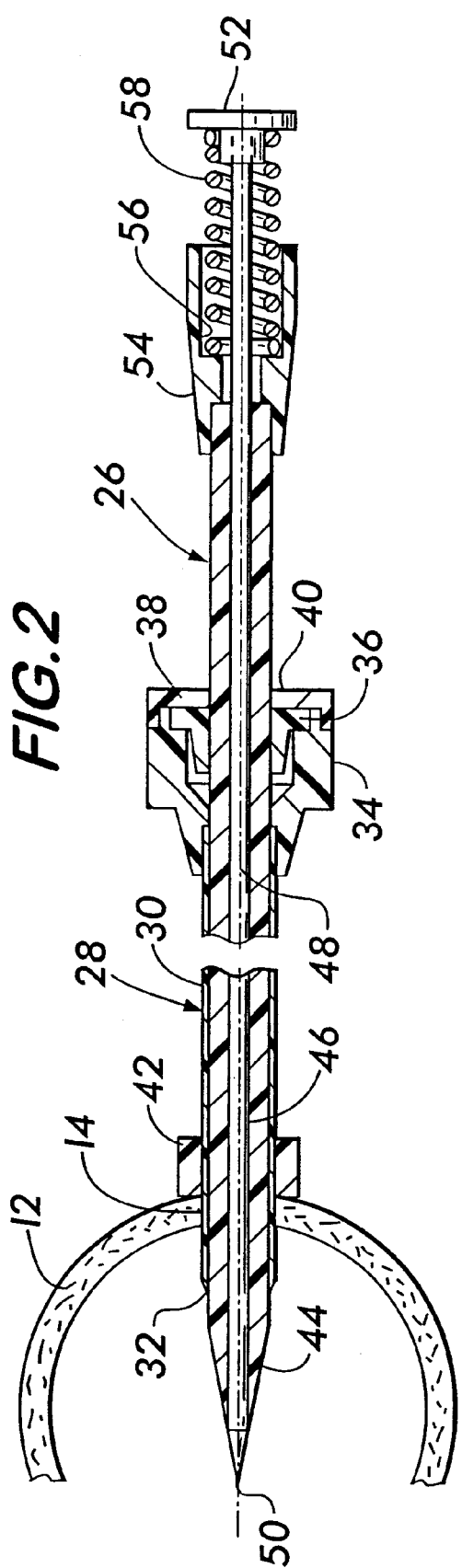
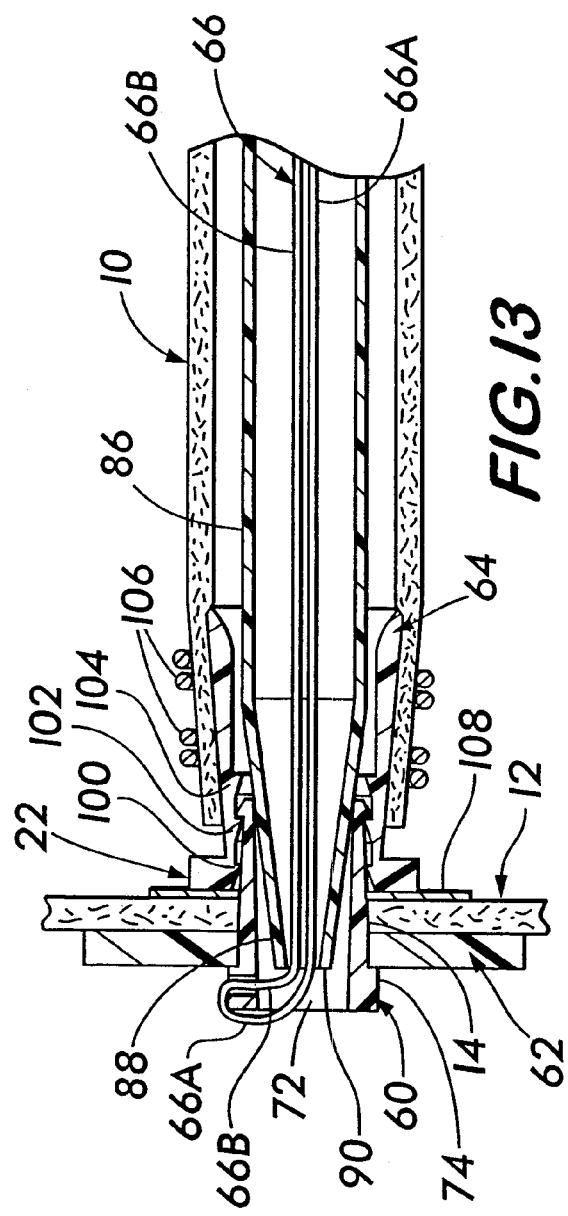

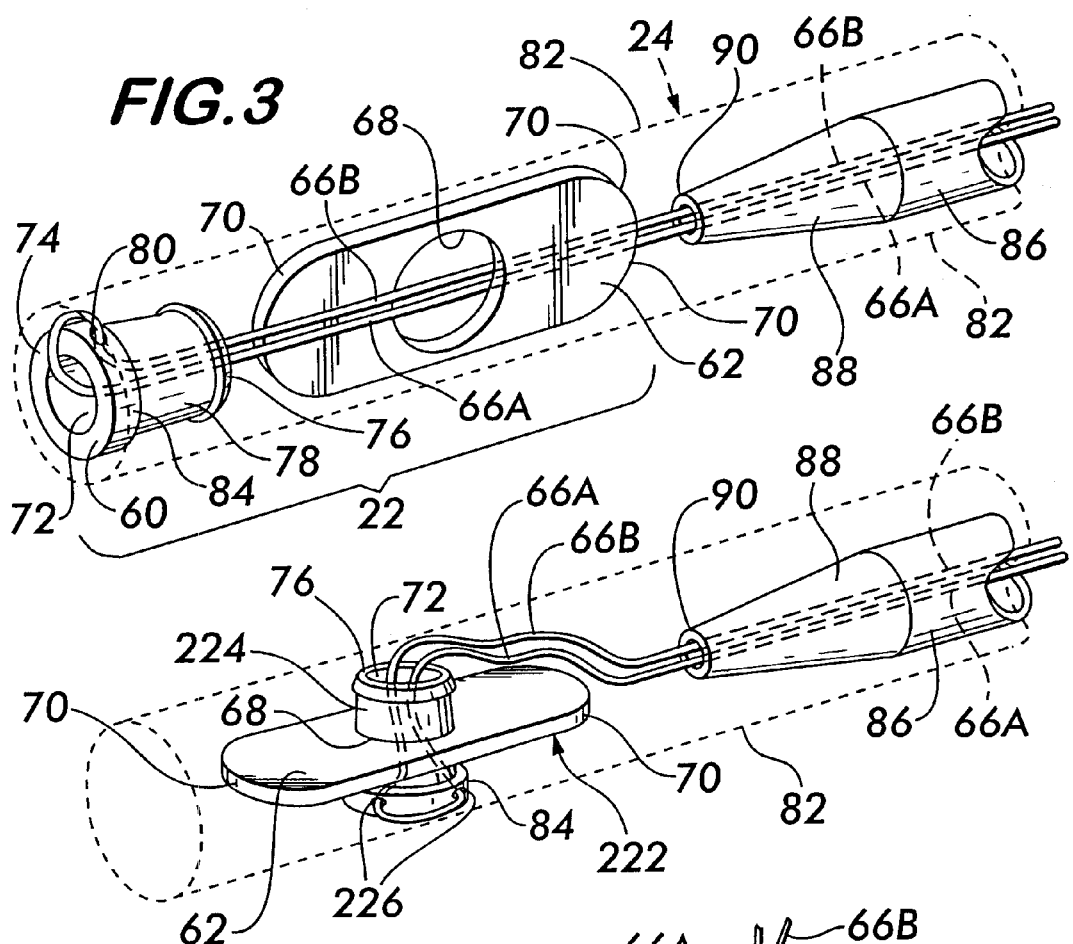
FIG.3
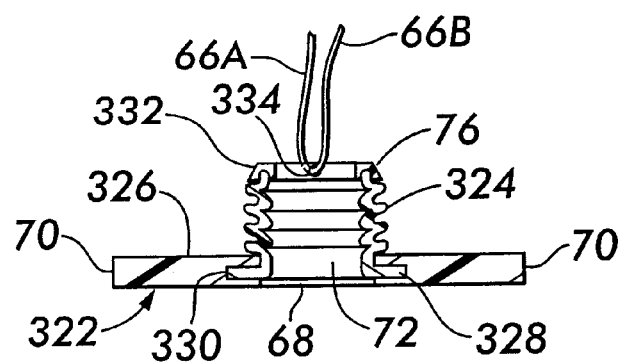
FIG.4
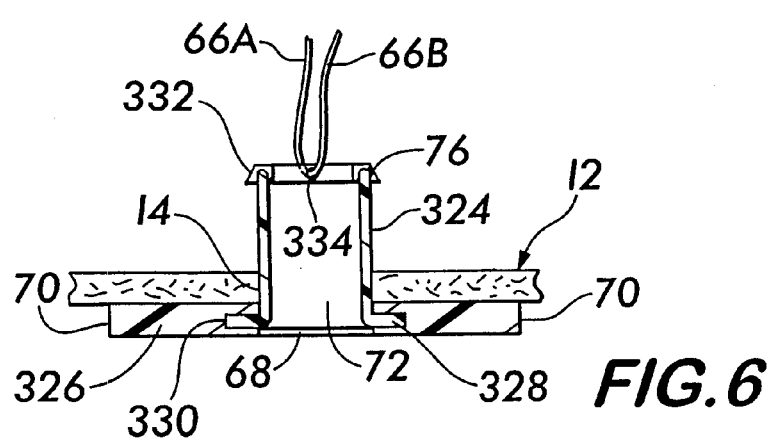
FIG.5
FIG.6

SURGICAL CONNECTOR SYSTEMS AND METHODS OF USE

RELATED APPLICATIONS

This application is a Continuation of our earlier filed U.S. Pat. Application, Ser. No. 08/923,682 on Sep. 4, 1997, entitled Connector System For Vessels, Ducts, Lumens or Hollow Organs And Methods Of Use, now U.S. Pat. No. 6,063,114, which is assigned to the same assignee as this invention and whose disclosure is incorporated by reference herein.

BACKGROUND OF THE INVENTION

This invention relates generally to medical devices and methods of performing surgical procedures and more particularly to the anastomosis of blood vessels, ducts, lumens or other tubular organs.

Arterial bypass surgery is a common modality for the treatment of occlusive vascular disease. Such surgery typically involves a formal surgical incision and exposure of the occluded vessel followed by the joinder of a graft, e.g., a mammary artery, saphenous vein, or synthetic graft (all collectively referred to hereinafter as the "bypass graft"), to the occluded vessel(hereinafter the "native" blood vessel) distally (downstream) of the occlusion. The upstream or proximal end of the bypass graft is secured to a suitable blood vessel upstream of the occlusion, e.g., the aorta, to divert the flow of blood around the blockage. Other occluded or diseased blood vessels, such as the carotid artery, may be similarly treated. Moreover, similar procedures are conducted to place a graft between an artery and a vein in dialysis patients.

While such surgical procedures are widely practiced they have certain inherent operative limitations. For example, sewing the graft to the host vessel, known as anastomosis, requires complex and delicate surgical techniques to accomplish the optimum result. Various complications must be avoided when anastomosing a bypass graft, whether it be a natural graft or a synthetic graft. For example, it is important that the juncture between the native vessel and the bypass graft form a smooth uniform transition without narrowing or regional irregularities which could tend to reduce blood flow. Moreover, any protuberances into the lumen could obstruct blood flow and may produce turbulence, thereby increasing the risk of clotting and/or restenosis. In addition, the difference in size between the typically larger internal diameter of the bypass graft and the typically smaller native artery may also produce unwanted turbulence in the blood. All of these characteristics can greatly diminish the effectiveness and patency of the graft.

Various devices and methods of use have been disclosed for effecting anastomosis of blood or other vessels, ducts, lumens or other tubular organs. Examples of such devices and methods are found in U.S. Pat. No. 2,127,903 (Bowen), U.S. Pat. No. 3,155,095 (Brown), U.S. Pat. No. 3,588,920 (Wesolowski), U.S. Pat. No. 3,620,218 (Schmitt et al.), U.S. Pat. No. 3,683,926 (Suzuki), U.S. Pat. No. 4,214,586 (Mericle), U.S. Pat. No. 4,233,981 (Schomacher), U.S. Pat. No. 4,366,819 (Kasler), U.S. Pat. No. 4,368,736 (Kasler), U.S. Pat. No. 4,470,415 (Wozniak), U.S. Pat. No. 4,501,263 (Harbuck), U.S. Pat. No. 4,675,008 (Tretbar), U.S. Pat. No. 4,512,761 (Raible), U.S. Pat. No. 4,552,148 (Hardy, Jr. et al.), U.S. Pat. No. 4,721,109 (Healy), U.S. Pat. No. 4,753,236 (Healy), U.S. Pat. No. 4,769,029 (Patel), U.S. Pat. No. 4,851,001 (Taheri), U.S. Pat. No. 4,816,028 (Kapadia et al.), U.S. Pat. No. 4,854,318 (Solem et al.), U.S. Pat. No. 4,930,502 (Chen), U.S. Pat. No. 4,931,057 (Cummings et al.), U.S. Pat. No. 4,957,499 (Lipatov et al.), U.S. Pat. No. 5,156,619 (Ehrenfeld), U.S. Pat. No. 5,123,908 (Chen), U.S. Pat. No. 5,192,289 (Jessen), U.S. Pat. No. 5,250,058 (Miller), U.S. Pat. No. 5,222,963 (Brinkerhoffet al.), U.S. Pat. No. 5,330,490 (Wilk et al.), U.S. Pat. No. 5,346,501 (Regula et al.), U.S. Pat. No. 5,364,389 (Anderson), U.S. Pat. No. 5,399,352 (Hanson), U.S. Pat. No. 5,425,738 (Gustafson et al.), U.S. Pat. No. 5,425,739 (Jessen), U.S. Pat. No. 5,443,497 (Venbrux), U.S. Pat. No. 5,445,644 (Pietrafitta et al.), U.S. Pat. No. 5,447,514 (Gerry et al.), U.S. Pat. No. 5,456,712 (Maginot), U.S. Pat. No. 5,456,714 (Owen), U.S. Pat. No. 5,503,635 (Sauer et al.), U.S. Pat. No. 5,509,902 (Raulerson), U.S. Pat. No. 5,571,167 (Maginot), U.S. Pat. No. 5,586,987 (Fahy) and U.S. Pat. No. 5,591,226 (Trerotola et al.).

In our copending U.S. patent application Ser. No. 08/861,584 filed on May 22, 1997 entitled Anastomosis System And Method of Use, which is assigned to the same assignee as this invention and whose disclosure is incorporated by reference herein, there is disclosed and claimed anastomosis systems and methods of use which overcome many of the disadvantages of the prior art.

OBJECTS OF THE INVENTION

It is a general object of this invention to provide connection, e.g., anastomosis, systems for vessels, ducts, lumens or hollow organs, and methods of use which furthers the state of the art.

It is a further object of this invention to provide a system and method of use for quickly, easily and safely effecting the anastomosis of vessels, ducts, lumens or other hollow or tubular organs.

It is a further object of this invention to provide a system and method of use for quickly, easily and safely effecting the formation of a fluid access port in vessels, ducts, lumens or other hollow or tubular organs.

It is a further object of the invention to provide absorbable devices for effecting the anastomosis of vessels, ducts, lumens, or other hollow or tubular organs.

It is a further object of the invention to provide absorbable devices for effecting the formation of a fluid access port in vessels, ducts, lumens, or other hollow or tubular organs.

It is a further object of this invention to provide a connector device for effecting the anastomosis of vessels, ducts, lumens or other hollow or tubular organs or for forming a fluid access port in vessels, ducts or lumens and which device is arranged for quick and sure placement with minimal chance of error.

It is a further object of this invention to provide a device for joining the ends of interrupted tubes or tubular organs of various sizes and functions, including, but not limited to, arteries, veins, lymphatic ducts, oviducts, ureters, intestines and the like.

It is a further object of the subject invention to provide a system for rapidly connecting two tubular bodies, e.g., a bypass graft to a native artery, without the need for sutures.

It is a further object of this invention to provide an instrument system for effecting the quick and easy insertion of an anastomosis device into a vessel, duct, lumen or other hollow or tubular organ.

It is a further object of this invention to provide a connector device for forming a port in a vessel, duct, lumen or other hollow or tubular organ.

It is a further object of this invention to provide an instrument system for effecting the quick and easy insertion of a connector device for forming a port in a vessel, duct, lumen or other hollow or tubular organ.

It is a further object of this invention to provide a system for effecting the anastomosis of a coronary bypass graft, e.g., the anastomosis of a bypass graft to the aorta, which may be accomplished without stoppage of the heart.

SUMMARY OF THE INVENTION

These and other objects of the instant invention are achieved by providing a system for effecting the bypass or other anastomosis of a portion of one vessel, duct, lumen or other hollow or tubular organ within the body of a living being with another vessel, duct, lumen, or other tubular organ, e.g., a bypass graft. The one vessel, duct, lumen or tubular organ has a wall with an opening provided therein. The other vessel, duct, lumen or tubular organ has a free end portion.

The system comprises a positioning member, e.g., a filament, and first connector assembly for connecting the other vessel, duct, lumen, or tubular organ, e.g., a bypass graft, to the one vessel, duct, lumen or tubular organ, e.g., a native blood vessel, to establish a passageway for carrying fluid, e.g., blood, therebetween.

The first connector assembly basically comprises an anchor member and a first connector member. The first connector member, e.g., a tubular flanged member, has a free end portion. The first connector member and the anchor member are coupled together and to the positioning member, e.g., the filament, and are movable relative to each other.

The anchor member and the first connector member are arranged to be introduced through the opening in the wall of the one vessel, duct, lumen or tubular organ, e.g., the aorta. The positioning member, e.g., the filament, is arranged to move, e.g., pull, the anchor member into engagement with tissue adjacent the opening in the wall of the one vessel, duct, lumen or tubular organ, and to move a portion of the first connector member into cooperative engagement with the anchor member and with the free end portion of the first connector member extending out through the opening in the one vessel, duct, lumen or tubular organ. The free end of the first connector member is arranged to be secured to the other vessel, duct, lumen or tubular organ (e.g., includes means to engage cooperating means mounted on the free end of the other vessel, duct, lumen or tubular organ) to secure the two vessels, ducts, lumens or tubular organs together.

In accordance with one preferred aspect of this invention the system includes a deployment instrument, e.g., a carrier tube holding the first connector member, the anchor member and the filament, and a guide/pusher member, for introducing the first connector member and the anchor member through the opening in the vessel, duct, lumen or tubular organ and for positioning it so that it is fixedly mounted therein, with the free end of the first connector member extending out of the opening in that vessel, duct, lumen or tubular organ.

In accordance with another aspect of this invention the first connector assembly also includes a second connector member for securement to the free end of the other vessel, duct, lumen or tubular organ, e.g., the bypass graft. The second connector member is arranged to be connected to the first connector member to secure the two vessels, duct, lumens or tubular organs together.

In accordance with another preferred aspect of the invention, the first connector assembly can be used to form a fluid access port in the one vessel, duct, lumen or tubular organ.

DESCRIPTION OF THE DRAWING

Other objects and many of the attendant advantages of this invention will become readily appreciated as the same becomes better understood by reference to the following detailed description when considered in connection with the accompanying drawing wherein:

FIG. 1 is a longitudinal sectional view of one embodiment of a first connector assembly and a deployment instrument which form a portion of the connector system of this invention for creating a fluid access port in a vessel, duct, lumen or tubular organ or for effecting the anastomosis between two vessels, ducts, lumens or tubular organs within the body of a living being;

FIG. 2 is a longitudinal sectional view of a piercing instrument and an introducer sheath also forming a portion of the connector system of this invention shown during the process of forming a small opening in the wall of the vessel, duct, lumen or tubular organ;

FIG. 3 is an enlarged, isometric view of the embodiment of the connector assembly of FIG. 1 shown in its "stowed" state disposed within the deployment instrument of this invention prior to its deployment;

FIG. 4 is an enlarged isometric view, similar to FIG. 3, but showing another embodiment of a connector assembly constructed in accordance with this invention and shown in its "stowed" state prior to its deployment;

FIG. 5 is a longitudinal sectional view showing yet another embodiment of a connector assembly constructed in accordance with this invention shown in its compact or "stowed" state prior to its deployment;

FIG. 6 is a longitudinal sectional view, similar to FIG. 5, but showing the embodiment thereof in its deployed state extending through an opening in the wall of a vessel, duct, lumen or tubular organ;

FIG. 13 is an enlarged longitudinal sectional view of the distal end of the deployment instrument of FIG. 12 during the anastomosis connecting procedure.

DETAILED DESCRIPTION OF PREFERRED EMBODIMENTS

Figure 7:
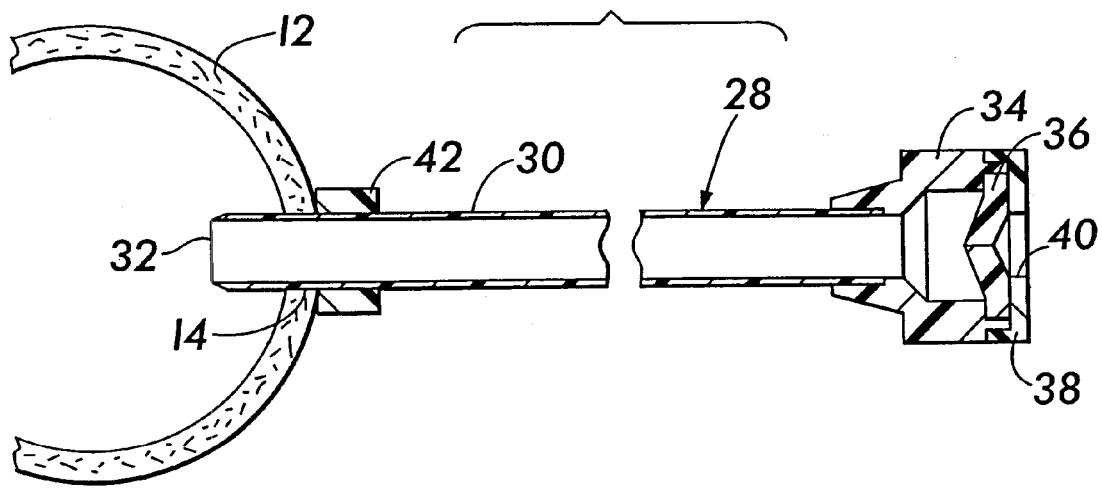
FIG. 7 is a longitudinal sectional view of the introducer sheath shown in FIG. 2 extending into an opening formed within a vessel, duct, lumen or tubular organ.

Referring now to the drawing wherein like reference characters refer to like parts, there is shown at 20 in FIG. 1 a connector system constructed in accordance with the subject invention.

Referring now to the various figures of the drawing wherein like reference characters refer to like parts, there is shown at 20 in FIG. 1 a connector system constructed in accordance with the subject invention. The system can be used to effect the anastomosis of any two vessels, ducts, lumens or tubular organs. In fact, the system 20 can be used to form a fluid access port in any vessel, duct, lumen or tubular organ.

Figure 14:
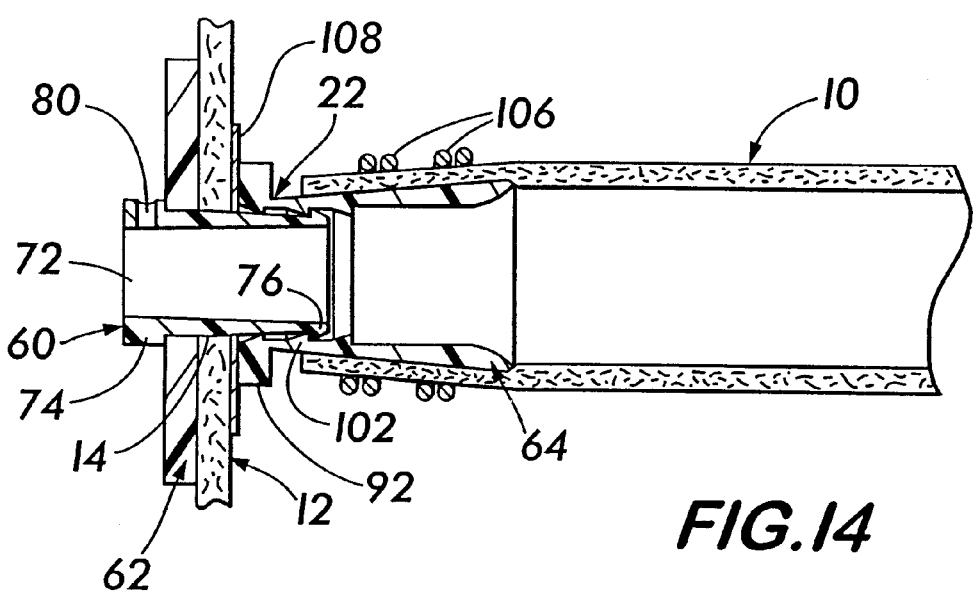
FIG. 14 is a longitudinal sectional view showing the completed anastomotic connection between the two vessels, ducts, lumens or tubular organs.

One particularly useful anastomosis application of the subject system is for effecting the bypass of an occluded coronary artery. This may be accomplished by forming an anastomotic connection between a saphenous vein graft and the aorta upstream of the occluded coronary artery. The completed anastomotic connection between the bypass graft and the aorta is shown in FIG. 14, wherein the bypass graft is designated by the reference numeral 10 and the aorta by the reference numeral 12.

The system basically comprises a first connector assembly 22 (FIGS. 1 and 14), a deployment instrument 24 (FIGS. 1 and 12), a piercer-dilator instrument 26 (FIG. 2) and an introducer sheath 28 (FIGS. 2 and 7). The deployment instrument 24 will be described in considerable detail later. Suffice it for now to state that the instrument 24 is arranged to house a portion of the connector assembly 22 therein and to deploy it within an opening formed in the wall of the vessel, duct, lumen or tubular organ so that a fluid access port or an anastomosis connection can be completed. As will also be described later, the deployment instrument 24 is arranged to be used after the piercer-dilator instrument (or some other means not shown) has formed a small opening 14 (FIG. 2) in the wall of the vessel, duct, lumen or tubular organ 12 to which the fluid access port or anastomosis connection is to be made and the introducer sheath 28 has been located within that opening.

Before describing the details of the piercer-dilator instrument 26, a brief description of the introducer sheath 28 is in order. To that end, as can be seen best in FIG. 7, the introducer sheath is of generally conventional construction and includes an elongated tubular body 30, e.g., an 8–14 French tube. The tubular body is formed of a biocompatible material, such as plastic, and has an open distal end 32 and closed proximal end 34. The proximal end 34 is closed by means of a conventional hemostasis valve housing including a resilient valve member 36 disposed therein. A sealing cap 38 holds the valve member 36 in place and includes a central opening 40 through which any suitable elongated member or instrument can be passed through the valve member 36 and the associated tube 30. As will be described hereinafter the piercer-dilator 26 is extended through the introducer sheath 28 and those two devices are used together to form the small opening 14 in the vessel, duct, lumen or tubular organ. Once the opening 14 has been formed, the piercer-dilator is removed from the sheath 28 and the introducer instrument 24 with the connection assembly 22 therein is passed through the introducer sheath to deploy the connector assembly. In order to prevent excessive penetration of the piercer-dilator into the vessel, duct, lumen or tubular organ during the formation of the opening 14 in the wall thereof, the introducer sheath 28 includes an annular stop 42 closely adjacent its open distal end 32.

Turning now to FIG. 2, the details of piercer-dilator 26 will now be described. Thus, as can be seen therein, the piercer-dilator 26 basically comprises an elongated tubular body having a tapered distal end 44. A central passageway 46 extends down the entire length of the body 44. A needle-plunger 48 extends through the passageway and terminates at its distal end in a sharply pointed tip 50. The proximal end of the needle-plunger is in the form of an enlarged head or cap 52. A cup shaped member 54 is mounted on the proximal end of the tubular body 44 of the piercer-dilator 26. The cup shaped member 54 includes central bore recess 56 arranged to receive one end of a helical compression spring 58. The other end of the helical spring engages the under surface of the cap 52. The spring is normally in its uncompressed state. It is shown in FIG. 2 in its compressed state, i.e., the state wherein the plunger cap 52 is pressed in the distal direction with respect to the cup shaped member 54. This action causes the piercing point 50 of the plunger to extend out of the opening at the tapered distal end of the dilator body 44. It is in this condition that the piercer-dilator is used to form the small opening 14 in the wall of the vessel, duct, lumen or tubular organ to which the access port or anastomosis connection is to be made. To that end, the piercer-dilator 26 is introduced through the hemostasis valve in the introducer sheath 28 until its distal end extends slightly beyond the open free end 32 of the sheath 28. A stop (not shown) is provided to ensure that the tip of the needle-dilator body does not extend too far beyond the open end of the sheath. With the needle-dilator in place the plunger cap 52 is pressed, i.e., moved distally with respect to the body of the piercer-dilator, whereupon the piercing point 50 extends out of the piercer-dilator. The exposed pointed tip 50 of the piercer-dilator instrument is then brought into engagement with the outer surface of the vessel, duct, lumen or tubular body, e.g., the aorta 12, at which the opening 14 is to be formed. The introducer sheath and the piercer-dilator are then pushed distally in through the wall of the vessel, duct, lumen or tubular organ, whereupon a small opening is formed. Further pushing of the needle-dilator into the opening enlarges it as the flared conical surface of the distal free end of the dilator body 44. Further pushing in the distal direction on the piercer-dilator instrument 26 and the introducer sheath 28 as a unit causes the distal end of the introducer sheath to enter into the opening 14. The combined piercer-dilator instrument and the introducer sheath are pushed inward until the stop 42 engages the outer surface of the wall of the vessel, duct, lumen or tubular organ. At this point, no further penetration can be made. Thus, the stop prevents the piercing tip from engaging the wall of the vessel, duct or lumen opposite the opening 14. Once the opening has been formed, the piercer-dilator 26 can then be removed by retracting or pulling on it proximally to withdraw it out of the introducer sheath 28 while leaving the introducer sheath in place, such as shown in FIG. 7. The system 20 is now ready for the use of the deployment instrument 24 to deploy the connector assembly 22 through the opening 14 into the interior of the vessel, duct, lumen or tubular organ.

Before describing the details of the deployment instrument 24, a description of the connector assembly 22 is in order given. To that end, as can be seen clearly in FIGS. 1, 3, 9 and 11, the connector assembly 22 basically comprises a first connector member 60, an anchor member 62 and a second connector member. The first connector member and the anchor member are arranged to be deployed within the interior of the vessel, duct or lumen and then to be moved with respect to each other to assemble them in a manner whereupon the anchor member engages the interior of the vessel, duct, lumen or tubular organ contiguous with the opening 14 and a portion of the first connector member extends out through the opening 14 to provide a fluid access port or a connection point for the second connector member 64. In some applications, the first connector member and the anchor member can be used in and of themselves to form a fluid access port to the interior of the vessel, duct, lumen or tubular organ.

As can be seen clearly in FIG. 3, the first connector member 60 and the anchor member 62 are coupled together by a positioning member, e.g., a flexible filament 66. The filament is preferably in the form of a conventional resorbable monofilament suture (or if desired a non-resorbable suture).

The anchor member 62 is an elongated strip formed of a resorbable, somewhat rigid material, such as polyglactide, polyglycolide or copolymers thereof. Non-absorbable materials, e.g., stainless steel, can be used for the anchor member. Each end of the anchor member 62 is rounded at 70. The first connector member 60 basically comprises a tubular body, preferably formed of the same material as that forming the anchor 62, and having a central passageway 72 extending therethrough. One end of the tube 74 is in the form of an annular flange. The flange need not be annular, and thus may merely be a tab or projection. The other end of the tube is in the form of at least one undercut annular lip or detent 76 whose exterior surface is chamfered. The outer surface 78 of the tubular connector body 60 between the flange 74 and the detent 76 is somewhat conical, i.e., is in the form of a surface which tapers from the flange 74 to the detent 76. The maximum outer diameter of the detent 76 of the connector member 60 is just slightly larger than the inside diameter of the hole 68 in the anchor member 62. A small aperture 80 extends radially outward from the central passageway 72 of the first connector member 60 through the annular flange 74.

As best seen in FIGS. 1 and 3, the filament 66 includes a pair of sequentially located sections 66A and 66B. In particular, section 66A extends from the proximal end of the deployment instrument 24 down the interior of that instrument through the central opening 68 in the anchor member 60, through the central passage 72 in the first connector member 60 from whence it doubles back to merge with the filament section 66B. The section 66B extends through the aperture 80 back into the interior passageway 72 in the first connector member 60 and through the central opening 68 in the anchor member 62. From there the section 66B of the filament 66 extends in the proximal direction through the deployment instrument to the proximal end thereof.

As mentioned earlier, the details of the deployment instrument will be described later, suffice it for now to state that this instrument includes a carrier 82 in the form of a tubular body in which the anchor member 62 and the first connector member 60 of the connector assembly 22 are disposed. The carrier tube includes an open, free (distal) end 84. As can be seen in FIGS. 1 and 3, the first connector member 60 is disposed within the carrier tube 82 immediately adjacent the open distal end 84, while the anchor member 62 is disposed immediately proximally of the first connector member.

The deployment instrument 24 also includes a guide-pusher assembly located within the carrier tube. The guide pusher assembly includes a tubular guide-pusher member 86 having a conical distal portion end 88. The free end 90 of the guide-pusher member includes a small opening communicating with the hollow interior of the guide-pusher and through which the filament sections 66A and 66B extend. The end 90 of the pusher member 86 is located immediately adjacent the proximally located rounded distal end 70 of the anchor member 62, when the anchor member is within the carrier tube in place as shown in FIGS. 1 and 3.

Deployment of the first connector member 60 and anchor member 62 is accomplished by operating the guide-pusher assembly, as will be described later, to cause the guide-pusher member 86 to push on the proximal end portion 70 of the anchor member 62 which in turn pushes on the distally located connector member 60 to expel the first connector member 60 out of the open free end 84 of the carrier member and out of the open end 32 of the introducer sheath 28 into the interior of the vessel, duct, lumen or tubular organ. Continued pushing on the guide pusher 86 in the distal direction then ejects the anchor member 62 into the interior of the vessel, duct, lumen or tubular organ.

Figure 9:
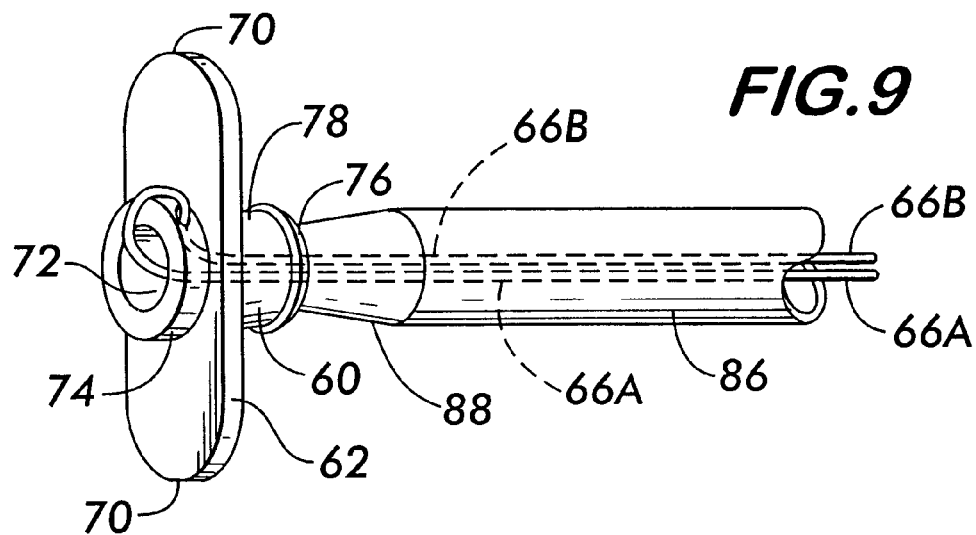
FIG. 9 is an isometric view of the connector assembly of FIG. 1, shown being assembled in its "deployed" state.
Figure 10:
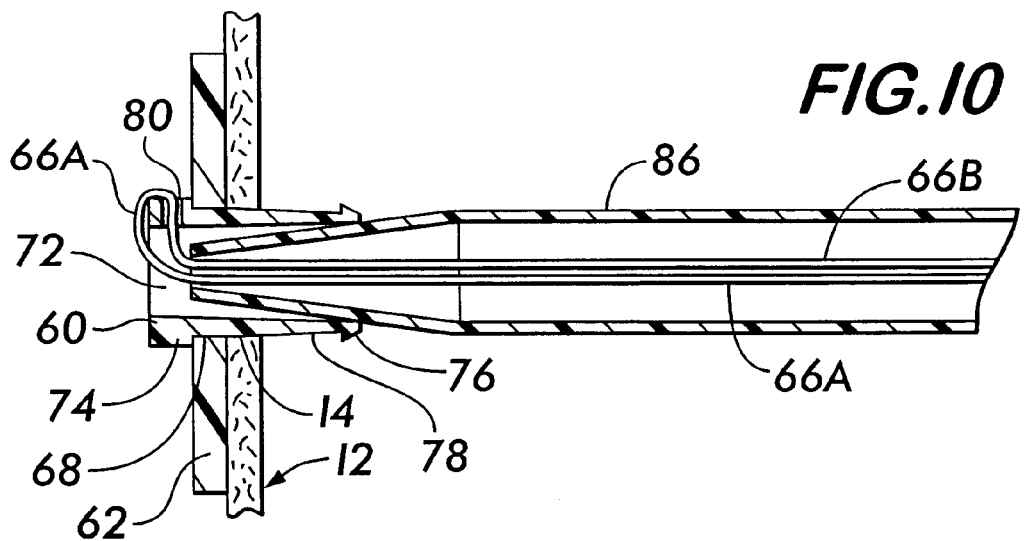
FIG. 10 is a longitudinal sectional view of the connector assembly of FIG. 1 shown during the deployment thereof in the opening in the wall of the vessel, duct, lumen or tubular organ.

In order to assemble the first connector member and anchor member and cause the detent end of the first connector member to be extended through the opening 14 in the wall of the vessel, duct, lumen or tubular organ, the two extending sections 66A and 66B of the filament 66 are retracted in the proximal direction, by means forming a portion of the instrument 24 to be described later. In particular, this retraction action on the filament sections pulls the first connector member toward the anchor member, whereupon the chamfered surface 76 of the first connector member enters into the central opening 68 in the anchor member. Continued retraction on the filament causes the anchor member to engage the interior surface of the vessel, duct, lumen or tubular organ contiguous with the opening 14 with the central opening 68 in the anchor member overlying the opening 14. Continued retraction of the two filament sections pulls the first connector member further into the central opening 68 in the anchor member, whereupon the portions of the anchor member contiguous with the central opening ride up the surface 78 of the first connector member until the flange 74 of the first connector member abuts the distally directed top surface of the anchor member 62, as shown in FIGS. 9 and 10. The retraction of the first connector member through the central opening 68 in the anchor member 62 causes the chamfered proximal end of the first connector member to pass through the opening 14 in the wall of the vessel, duct, lumen or tubular organ 12, as shown in FIG. 10. During the retraction of the filament sections 66A and 66B, the guide-pusher member 86 remains stationary so that its tapered distal end 88 enters into the central passageway 72 of the first connector member 60 when the first connector member is pulled through the opening 14 in the wall of the vessel, duct, lumen or tubular organ. Thus, the tapered end of the guide-pusher member 86 serves to guide or orient the first connector member 60 so that its central longitudinal axis is disposed generally perpendicularly to the wall of the vessel, duct, lumen or tubular organ 12, as shown in FIG. 10.

Figure 11:
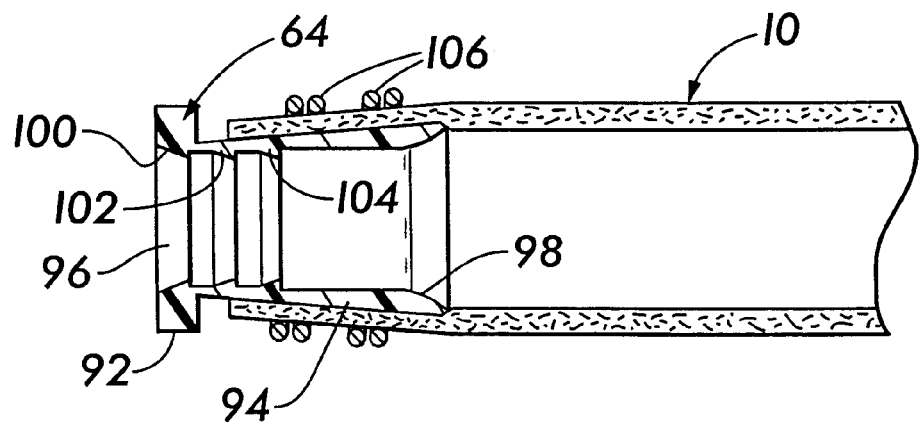
FIG. 11 is a longitudinal sectional view of another connector component forming another portion of the connector assembly of FIG. 1 and with a second vessel, duct, lumen or tubular organ secured thereto for forming an anastomotic connection between the two vessels, ducts, lumens or tubular organs.

With the first connector member 60 and the anchor member 62 deployed as shown in FIG. 10, the system is now ready to complete the anastomosis. To that end, the second connector member 64 is pre-mounted on the distal end of any desired vessel, duct, lumen or tubular organ like that shown in FIG. 11. For example, as shown in FIG. 11, the connector 64 can be disposed and secured within the open distal end of a saphenous vein bypass graft 10. The second connector member basically comprises a hollow tubular member, formed of the same material as that of the first connector 60 and the anchor member 62. The distal end of the second connector 64 is in the form of an annular flange 92. The outer surface of the tubular connector 64 proximally of the flange 92 is in the form of a slightly outwardly tapering conical surface 94, i.e., a surface whose diameter increases linearly in the proximal direction. A central passageway 96 extends through the length of the connector member 64, the proximal end of the passageway 96 forms a flared throat 98. Three annular undercut detent rings 100, 102 and 104 extend about the inter-periphery of the central passageway 96 at closely spaced locations adjacent the flanged distal end 92 of the connector 64. The outer surface of each of these detents is chamfered and is arranged to cooperate and engage the chamfered surface of the detent 76 of the first connector member 60 to lock the two connector members together, as will be described later. The flared proximal end of the second connector 64 is located within the hollow interior lumen of the bypass graft 10 and is secured in place therein by plural stainless steel springs 106. The springs extend about the periphery of the distal end of the bypass graft to interpose that portion of the bypass graft tightly between the springs and the exterior surface 94 of the second connector member 64. Thus, the second connector member is fixedly secured to the distal end of the bypass graft.

The bypass graft with the second connector member fixedly secured thereto as shown in FIG. 11 is arranged to be deployed or slid down over the deployment instrument 24, as will be described later, and over the guide-pusher member 86 like shown in FIG. 13, whereupon the flange 92 of the second connector member 64 abuts the exterior surface of the vessel, duct, lumen or tubular organ contiguous with the opening 14 therein. The undercut surface of the detent surface 76 of the first connector member engages one of the undercut surfaces of the three chamfered detent rings 100, 102 or 104, with the particular detent being engaged being dependent upon the thickness of the wall of the vessel, duct, lumen or tubular organ.

In the embodiment shown in FIG. 13, the undercut portion of the detent 76 of the first connector member 60 engages the undercut portion of the detent ring 102 of the second connector member 64. This action effectively sandwiches the wall of the vessel, duct, lumen or tubular organ between the flange 92 of the second connector member 64 and the anchor member 62, thereby fixedly securing the connector assembly 22 in place within the opening 14, thereby completing the anastomosis.

In accordance with a preferred embodiment of this invention, a washer 108 is interposed between the flange 92 of the second connector member 64 and the outer surface of the wall of the vessel, duct, lumen or tubular organ contiguous with the opening 14 to prevent bleeding at the interface of the connector assembly and the opening 14 in the wall of the vessel, duct, lumen or tubular organ. The washer is preferably formed of a hemostatic material, e.g., collagen.

As should be appreciated from the previous discussion, the embodiment of the connector assembly 22 described heretofore makes use of components which are coupled together, but not assembled. By that it is meant that the components are disposed with respect to each other so that they are held in a compact configuration within the carrier tube for expulsion into the interior of the vessel, duct, lumen or tubular organ. Once expelled they are movable or positionable with respect to each other and with respect to the wall of the vessel, duct, lumen or tubular organ to assemble them in their "deployed state." In the deployed state the portions are oriented with respect to each other so that they are resistant to accidental dislodgement within the opening in the wall of the vessel, duct, lumen or tubular organ. In particular, the anchor member, lying against the interior wall of the vessel, duct, lumen or tubular organ contiguous with the opening prevents the deployed connector assembly from falling out of that opening.

In FIG. 4 there is shown an alternative embodiment of a connector assembly 222 constructed in accordance with this invention. The assembly 222 is similar in many respects to the connector assembly 22, but in other ways differs. In this connection, the connector assembly 222 includes components which are preassembled so that they are connected to each other prior to deployment. These preassembled components are held in a compact or "stowed" state within the carrier tube 82 so that they can be ejected from the carrier tube as a unit into the interior of the vessel, duct, lumen or tubular organ. Once ejected, the connector assembly 222 can then be retracted in a similar manner to that described heretofore to bring a portion of it into engagement with the wall of the vessel, duct, lumen or tubular organ contiguous with the opening 14 while another portion extends out to that opening for connection to the second connector member 64. The connector assembly 222 basically comprises a first connector member 224, an anchor member 62 and a second connector member 64. The anchor member 62 and the second connector member are identical to those components making up the connector assembly 22. Thus, in the interest of brevity, the details of the anchor component 62 and the second connector component 64 will not be reiterated and the various portions of these components will be given the same reference numerals as given previously.

The first connector member 224 is preferably formed of the same material as that of the anchor member 62. Moreover, the first connector member 224 includes various portions which are constructed similar to the connector member 60 of connector assembly 22. Thus, in the interest of brevity, the portions of the first connector assembly 224 which are similar to those portions of the first connector 60 will be given the same reference numerals. In particular, the first connector member 224 is a tubular member having a central passageway 72 extending through it. The distal end of the connector member 224 is in the form of an annular flange 84 while the proximal end is in the form of a chamfered surface detent 76. The outer surface of the connector between the flange 84 and the detent 76 is of circular profile and extends through the central opening 68 in the anchor member 62 so that the connector member 224 is slidable longitudinally within that opening. The connector assembly 222 is arranged to be disposed in a compact or "stowed" position within the carrier tube 82 of the deployment instrument. In particular, the connector 224 is centered within the opening 68 in the anchor 62, as shown in FIG. 4 to ensure that it has the smallest cross sectional profile for disposition within the carrier tube.

A pair of apertures 226 extend radially inward through the flange 84 to enable the filament 66 to be coupled to the connector member 224. In particular, the filament section 66B extends through the open proximal end of the central passage 72 of the connector member 224 and out through one of the apertures 226. The filament section 66B extends into the other aperture 226. From that point, the filament section 66B extends through the passageway 72 and out the proximal end thereof. The proximal end portions of filament sections 66A and 66B extend through the guide-pusher and through the deployment instrument, as will be described later.

Deployment of the connector assembly 222 is accomplished in a similar manner to that of connector assembly 22. In this regard, the guide-pusher assembly is used to push the assembled connector 224 and anchor 62 out of the carrier tube so that the preassembled connector member 24 and the anchor member 62 are located within the interior of the vessel, duct, lumen or tubular organ. Retraction of the filament sections 66A and 66B brings the proximal end of the connector member 224 back through the opening 14 in the wall of the vessel, duct, lumen or tubular organ. Moreover, retraction of the filament sections causes the top or proximal surface of the anchor member 62 to move into engagement with the inner surface of the vessel, duct, lumen or tubular organ contiguous with the opening 14, thereby causing the anchor member to "hang-up" on that surface. Further, retraction of the filament sections moves the connector member 224 with respect to the anchor member, i.e., it causes the connector member to slide through the hole 68 in the anchor member, so that more of the connector member 224 extends out of the opening in the wall of the vessel, duct, lumen or tubular organ until its flange 84 engages the bottom or distal surface of the anchor member contiguous with the hole 68. At this time, the connector device 224 is fully deployed and ready for connection to the connector member 64 and the bypass graft 10 connected to that connector. That connection is accomplished in the same manner as with the connector assembly 22 described earlier.

In FIG. 5, there is shown another alternative embodiment 32 of a connector assembly constructed in accordance with this invention. The connector assembly 322 is somewhat similar to the connector assembly 222 in that it is preassembled, i.e., its first connector and anchor components are assembled or connected to each other, but are movable relative to each other during the deployment procedure. In the interest of brevity, the common components of the connector assembly 322 and connector assembly 222 and connector assembly 22 will be given the same reference numerals and the details of their construction and operation will not be reiterated. Thus, as can be seen in FIG. 5, the connector assembly 322 basically comprises a first connector member 324 and an anchor member 326. The first connector member 324 and the anchor member 326 are an integral unit, with the anchor unit 326 being similar in construction to the anchor member 62. Thus, the anchor member includes a central hole 68. The first connector member 324 is a collapsible, e.g., a corrugated, tube having a central passageway 72 extending therethrough. The distal end of the corrugated tube 324 is in the form of a flange 328 which is received within a correspondingly shaped annular recess 330 extending about the hole 68 in the anchor member 326. The tube 324 is arranged to be held in its compact or "stowed" state as shown in FIG. 5 when it is within the carrier tube of the deployment instrument, and to be extended to its deployed state, as shown in FIG. 6, during its deployment.

The proximal end of the collapsible corrugated tube 324 is in the form of an annular collar 332 forming a detent having a chamfered surface 76. The collar 332 is fixedly secured to the proximal end of the corrugated tube 324.

The anchor member 326 is preferably formed of a resorbable material, like that of the anchor members described heretofore. The corrugated tube may also be formed of the same resorbable material. Alternatively, it may be formed of any conventional biocompatible material, such as Dacron mesh, providing that it is impervious to the flow of liquid through it so that fluid flowing through the central passageway 72 will not leak out the wall of the corrugated tube 324 much like a synthetic vascular graft.

A radially oriented aperture 334 is provided in the annular collar 332 through which the filament 66 extends so that one filament section 66B extends from one side of the aperture while the other filament section 66A extends from the other.

The connector assembly 322 is disposed within the carrier tube 82 in its compact state like that shown in FIG. 5, so that its anchor member is oriented parallel to the central longitudinal axis of the carrier tube and immediately distally of the distal end 90 of the guide-pusher member 86. The filament sections 66A and 66B extend back through the interior of the guide-pusher and through the deployment instrument. The connector assembly 322 is ejected from the carrier tube in the same manner as described with reference to the connector assemblies 22 and 222. Once ejected into the interior of the vessel, duct, lumen or tubular organ, the two filament sections 66A and 66B are retracted. As will be described later, to draw the collar 332 of the connector assembly 332 back through the opening 14 in the wall of the vessel, duct, lumen or tubular organ. Continued retraction of the filament sections cause the top or proximal surface of the anchor member 326 to engage the interior surface of the vessel, duct, lumen or tubular organ contiguous with the opening 14 to cause it to hang-up in the same manner as described earlier. Once the anchor hangs-up, continued retraction of the filament section cause the corrugated tube 324 to stretch or straighten out, thereby increasing the length of the tube from the state shown in FIG. 5 to the state shown in FIG. 6. Once the connector assembly 322 is in the fully deployed state shown in FIG. 6, the second connector member 64 and the bypass graft 10 connected to it can be secured to the assembly 322 in the same manner as described heretofore.

Figure 12:
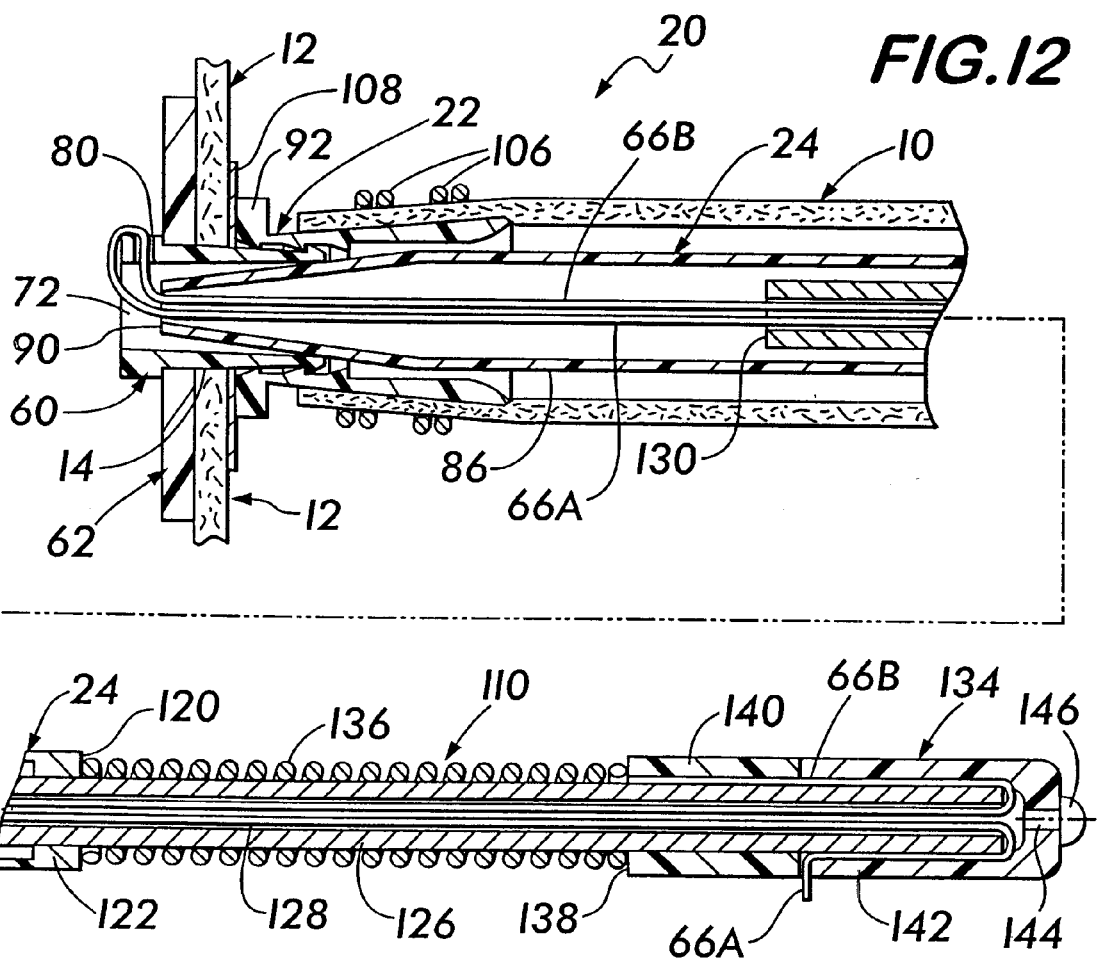
FIG. 12 is a longitudinal sectional view of the deployment instrument of FIG. 1 showing the formation of the anastomosis connection between the two vessels, ducts, lumens or tubular organs.

Referring now to FIGS. 1 and 12, the details of the deployment instrument 24 will now be described. Thus, as can be seen the deployment instrument 24 basically comprises the heretofore identified carrier tube 82 and the heretofore described pusher-guide assembly. That assembly includes the pusher-guide member 86 and an actuation assembly 110.

The carrier tube 84 includes an annular ring or stop 112 secured about is outer periphery immediately adjacent the proximal end 114. The stop 112 is provided to ensure that the carrier tube of the deployment instrument is not extended too far into the introducer sheath 28. Thus, the stop is arranged to engage the rear wall 38 of the hemostasis valve when it is in proper position.

The proximal end 114 of the guide tube is in the form of an inwardly extending, annular wall 116 having a central passageway 118 therein. The passageway 118 is adapted to closely receive the outer surface of the cylindrical portion of the pusher-guide member 86 to form a generally fluid-tight seal therebetween. The proximal end 120 of the pusher-guide member 86 is in the form of an inwardly extending annular wall 122 having a central passageway 124 therein. The central passageway 124 is arranged to closely receive a portion of the actuation assembly 110 (to be described hereinafter) to form a generally fluid tight seal therebetween.

The actuation assembly 110 basically comprises an elongated cylindrical mandrel rod 126 having a central passageway 128 extending along its length between its open distal end 130 and its open proximal end 132. The passageway 128 communicates with the interior of the pusher-guide member 86. An actuation cap 134 is mounted on the proximal end of the mandrel rod, with a helical compression spring 136 extends about the outer periphery of the hollow mandrel rod 126 interposed between the proximal end 120 of the pusher-guide tube 86 and a stop surface 138 forming the distal end of the actuation cap 134. The cap 134 basically comprises a pair of hollow tubular sections 140 and 142. The section 142 is disposed proximally of section 140 and is cup-shaped. The section 140 is fixedly secured to the mandrel rod 126 with the distal end of the filament section 66B tightly interposed therebetween. In particular, filament sections 66A and 66B extend from the connector assembly 22 through the pusher-guide member 86 into the hollow interior of the mandrel rod 126 and out the proximal end opening 132 of the passageway 128 extending through the mandrel rod 126. The distal end portion of filament 66B extends under the cup-shaped cap section 142 and is trapped between the outer surface of the mandrel rod 126 and the inner surface of the cap shaped 140. The distal end of the filament section 66A also extends out the proximal end 132 of the passageway 128 and is trapped between the outer surface of the mandrel tube 128 and the inner surface of the cup-shaped portion 142 of the cap 134. The cup-shaped portion 142 of the cap is removable for reasons to be described later.

The cap 134 also includes a central aperture in its end wall in communication with the interior passageway 128 of the mandrel tube 126. A plug, formed of a resilient material, such as rubber, is releasably located within the aperture 144 to seal it. The aperture 144, with the plug removed serves as a means to enable the deployment instrument 24 to determine the location of the wall of the vessel, duct, lumen or tubular organ as will be described later.

Figure 8:
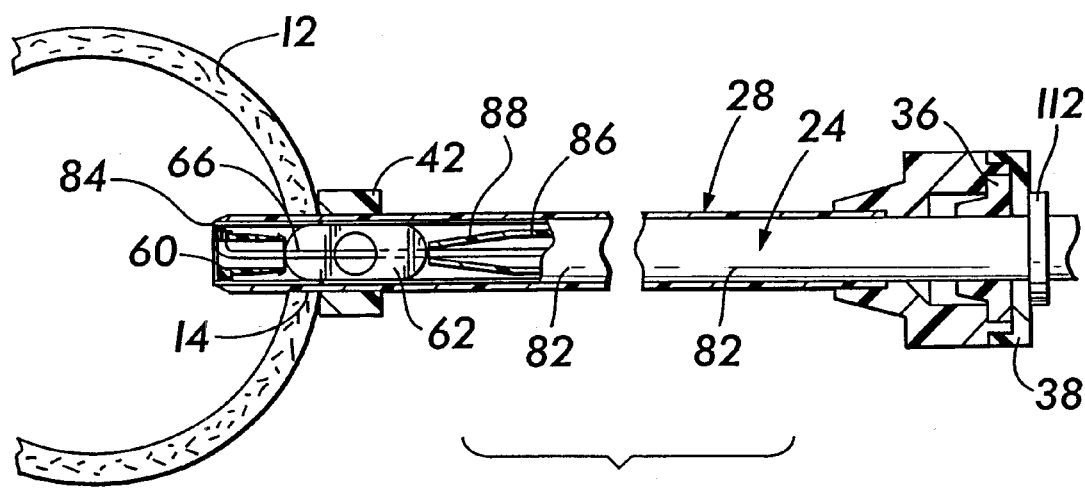
FIG. 8 is a longitudinal sectional view, similar to FIG. 7, but showing the deployment instrument extending through the introducer sheath to deploy the connector assembly of FIG. 1 into the interior of the vessel, duct, lumen or tubular organ.

Operation of the deployment instrument 24 is as follows:

The instrument is inserted into the introducer sheath after the sheath has been positioned with the piercer-dilator to form the opening 14 in the wall of the vessel, duct, lumen or tubular organ and the piercer-dilator has been removed. To that end, the deployment instrument is extended through the introducer sheath which is positioned as shown in FIG. 7 until the stop ring 112 on the deployment instrument 24 abuts the proximal end 38 of the hemostasis valve of the introducer sheath 28, as shown in FIG. 8. The cap 134 of the actuation assembly 110 is then pushed in the distal direction, thereby imparting movement in the distal direction to the pusher-guide tube 86 via the interposed spring 136. This action causes the free distal end 90 of the guide-pusher member to engage the proximal end of the anchor member 64 of the connector assembly 22 within the carrier tube 82. Continued pushing on the cap in the distal direction causes the pusher-guide member to eject the first connector member 60 and the anchor member 62 as described heretofore. Once the connector assembly's components are free of the guide tube and are located within the interior of the vessel, duct, lumen or tubular organ, the spring in attempting to assume its uncompressed natural state, applies tension to the filament sections 66A and 66B. In particular, the release of pressure on the cap 136 allows the spring to move from its compressed state shown in FIG. 1 to a longitudinally expanded or uncompressed state shown in FIG. 12. Since the filament ends are trapped by the cap 134, this action pulls the filament sections in the proximal direction, thereby drawing the components 60 and 62 of the first connector assembly 22 into the deployed state shown in FIGS. 9 and 10. Once the components are in this state, the introducer sheath is withdrawn, i.e., pulled off the instrument, leaving the deployment instrument 24 in the position shown in FIG. 12.

The second connector member 64 with the bypass graft 10 secured thereto is then threaded and slid down the instrument 24 over the actuation assembly and the pusher-guide tube to the position shown in FIG. 12. If a hemostatic washer 108 is used, as is preferable, that washer is threaded on the deployment instrument in advance of the second connector member 64.

When the second connector member 64 and the associated bypass graft 10 are slid in a distal direction until the flange 92 either directly engages the anchor surface of the wall of the vessel, duct, lumen or tubular organ or indirectly engages it via an interposed hemostatic washer 108. One of the chamfered detents of the second connector member 64 will be engaged by chamfered detent 76 of the first connector member 60 to secure the first and second connector members together.

Once the connector members 60 and 62 are connected together, the deployment instrument 24 can be removed to leave the anastomotic connection in position. To that end, the cup-shaped portion 142 of the actuating cap 134 is removed, thereby freeing the proximal end of filament section 66A. The remaining portion 142 of the cap 146 is then pulled or withdrawn in the proximal direction to withdraw the deployment instrument from within the interior of the bypass graft 10. Since the proximal end of filament section 66A is no longer trapped but the proximal end of the filament section 66B is trapped by the cap section 140 retraction of the instrument 24 causes the filament section 66A to move down the passageway 128 of the mandrel tube. Eventually, the free end of section 66A will pass through the aperture 80 in the first connector member 60 and from there will be pulled through the passageway 72 of that member and through the bypass graft interior until it exits the proximal end of the graft. At this point, the deployment instrument 24 will be fully removed from the anastomotic connection, leaving that connection in the state shown in FIG. 14.

The proximal end (not shown) of the bypass graft 10 can be secured to the occluded coronary artery (not shown) distally of the occlusion by any suitable technique. For example, the distal end of the bypass graft can be surgically connected to the coronary artery, or it can be connected utilizing means similar to that described herein introduced via an access port or slit (not shown) made in the wall of the bypass graft or by means such as taught in our co-pending United States patent application identified above.

As mentioned earlier, the actuation cap 134 of the deployment instrument 24 includes an aperture 144 which is sealed with a plug 146. The aperture 144 enables one to determine if the deployment instrument is properly positioned with respect to the wall of the vessel, duct, lumen or tubular organ. This action is accomplished by removing the plug 146 from the aperture so if the instrument is disposed at the desired position it will be in communication with the interior of the vessel, duct, lumen or tubular organ. Accordingly, blood will be enabled to flow from the interior of the vessel, duct, lumen or tubular organ and through the hollow interior of the pusher-guide member, and the communicating passageway in the mandrel tube where it exits the proximal end of that passageway and through communicating port 144. Thus, when a drop of blood or other fluid appears at the port, the user of the instrument 24 knows that the device is in the desired position. The plug 146 can then be reinserted into the aperture 144 to seal it so that no further blood can gain egress through the instrument 24.

It should be pointed out at this juncture that the piercer-dilator instrument 26 may be constructed to utilize a similar flashback construction to provide an indication of proper placement, by the egress of a drop of blood from the proximal end of the piercer-dilator. More likely, the formation of the opening in the wall of the vessel, duct, lumen or tubular organ will be preformed under direct vision. If a fluid flashback system is incorporated into piercer-dilator, or the introducer sheath, it will allow placement of the introducer sheath at a specific location within the vessel, duct, lumen or tubular organ without the need for direct observation.

It must be pointed out at this juncture that it is contemplated that the connector assemblies of this invention could be actively assembled or deployed by manual pulling of the filament sections and pushing on the pusher member instead of using a spring loaded system like described heretofore.

The bypass graft 10 is prepared by inserting the proximal end of the second connector member 64 into the open distal end of the graft section 10. The connector is held in place by use of one or more stainless steel spring clips 106. The spring clips and the second connector 64 are preferably available in different sizes to cater to different graft sizes. In particular, the spring clips 106 are sized to a predetermined inside diameter to limit the constriction of the graft which would otherwise cause necrosis of the interposed tissue due to excessive pressure. Other means can be utilized to secure the graft 10 to the second connector member 64. Such means may be a biocompatible adhesive, pre-knotted suture loops, sutures, c-clips, etc.

The inside profile of the passageways of the connector assemblies of this invention are preferably designed to minimize turbulence and control the pressure of fluid flowing therethrough, such as disclosed in our heretofore identified co-pending patent application. It should also be pointed out that the various connector components of the connector assemblies of this invention can be coated with, or impregnated with chemicals, drugs, or other biologically active components to affect the nearby tissue or cells. Such active components could include, but are not limited to, anti-platelet drugs, antimicrobial agents, antibiotics, anti-thrombogenic materials, anti-oxidants, growth factors, growth hormones, genetic material, or seeded cells.

It should be noted that the embodiments of the connector assemblies and/or the deployment instrument and/or the piercer-dilator instrument, and/or the introducer sheath as shown and described heretofore are merely exemplary. Thus, other constructions are contemplated. For example, the anchor member may be shaped other than a linear strip, e.g., it may be slightly arcuate or trough-shaped like that disclosed in our aforementioned copending application. The positioning member for the connector assemblies may comprise other types of components making use of at least one filament or may comprise other devices, such as a flexible wire having a balloon on its distal end. The connector assemblies and/or the components thereof need not be formed to be totally resorbable. Thus, none or only portions of such assemblies may be resorbable.

Without further elaboration the foregoing will so fully illustrate our invention that others may, by applying current or future knowledge, adopt the same for use under various conditions of service.

We claim:

1. A method bypassing a portion native blood vessel within the body of a living using a bypass graft, the native blood vessel having a wall with an opening provided therein, said method comprising:
   (A) providing an anchor member and a first connector member having a free end portion;
   (B) coupling said first connector member and said anchor member together so that they are movable relative to each other;
   (C) introducing said anchor member and said first connector member through the opening in the wall of the native blood vessel into the interior of the native blood vessel;
   (D) moving said anchor member within the interior of the native blood vessel into engagement with the wall of the native blood vessel adjacent the opening therein; and
   (E) moving a portion of said first connector member with respect to said anchor member to secure the first connector member to said anchor member and with said free end portion of said first connector member extending out through the opening in the native blood vessel so that said bypass graft can be secured thereto.

2. The method of claim 1 additionally comprising the step of mechanically securing said bypass graft to said free end portion of said first connector member.

3. The method of claim 2 additionally comprising the steps of:
   (F) providing a second connector member secured to said bypass graft; and
   (G) securing said first and second members together to secure said bypass graft to the native blood vessel.

4. The method of claim 1 additionally comprising the steps of:
   (F) providing a retraction member coupled to said anchor member and said first connector member;
   (G) extending said retraction member through the opening in the wall of the native blood vessel; and
   (H) pulling on said retraction member in a proximal direction to move said anchor member and said first connector member relative to each other.

5. The method of claim 4 wherein the pulling of said retraction member moves said anchor member within the interior of the native blood vessel into engagement with the wall of the native blood vessel adjacent the opening therein and moves said free end portion of said first connector member to a position extending out through the opening in the native blood vessel.

6. The method of claim 1 additionally comprising the step of:
   (G) providing a deployment instrument; and
   (H) utilizing said deployment instrument for delivering said anchor member and said first connector member through the opening in the wall of the native blood vessel.

7. The method of claim 1 additionally comprising the step of piercing the wall of the native blood vessel to form the opening in the native blood vessel.

8. The method of claim 7 wherein the step of piercing the wall of the native blood vessel is achieved by means of a piercing instrument.

9. The method of claim 8 additionally comprising the steps of:
   (G) providing a deployment instrument; and
   (H) extending said deployment instrument through the opening in the wall of the native blood vessel formed by said piercing instrument for delivering said anchor member and said first connector member therethrough into the interior of the native blood vessel.

10. A system for bypassing a portion native blood vessel within the body of a living being by use of a bypass graft, the native blood vessel having a wall with an opening provided therein, said system comprising a first connector assembly for connecting the bypass graft to the native blood vessel to establish a passageway for carrying blood therebetween, said first connector assembly comprising an anchor member and a first connector member, said first connector member and said anchor member being movably coupled together and arranged so that at least a portion of each is introduced through the opening in the wall of the native blood vessel into the interior thereof, said at least one portion of said anchor member being arranged to be moved within the interior of the native blood vessel into engagement with the wall of the native blood vessel adjacent the opening, said at least one portion of said first connector being arranged to be moved within the interior of the native blood vessel with respect to said anchor member, said first connector member having a free end portion arranged to be extended out of the opening in the native blood vessel while said at least one portion of said first connector is within the interior the native blood vessel, said free end of said first connector member being arranged to be secured to the bypass graft to secure the bypass graft to the native blood vessel.

11. The system of claim 10 additionally comprising a positioning member for moving said at least one portion of said anchor member and said at least one portion of said first connector member within the interior of the native blood vessel.

12. The system of claim 11 wherein said anchor member comprises an elongated member and having a connector-receiving opening arranged to receive a portion of said first connector member when said anchor member and said first connector member are moved with respect to each other.

13. The system of claim 12 wherein said first connector member comprises a tube having a lumen therein.

14. The system of claim 13 wherein said tube has a pair of ends, one of said ends having a flange and the other of said ends forming said free end of said first connector member, said tube being arranged to be drawn into said opening area of said anchor member, whereupon a portion of said flange abuts a portion of said anchor member.

15. The system of claim 10 additionally comprising a second connector member which is arranged to be connected to said free end of said first connector member.

16. The system of claim 15 wherein said second connector member comprises a tube and an abutment portion arranged to be disposed closely adjacent the outside of the native blood vessel contiguous with the opening therein when said first and second connector members are secured together.

17. The system of claim 16 wherein each of said first and second connector members includes means for enabling them to be snap fit together.

18. The system of claim 10 wherein said first connector assembly comprises at least one resorbable portion.

19. The system of claim 10 additionally comprising a deployment instrument for delivering said at least one portion of said anchor member and said at least one portion of said first connector member through the opening in the wall of the native blood vessel.

20. The system of claim 19 wherein said deployment instrument comprises a carrier tube having a lumen in which said anchor member and said first connector member are disposed.

21. The system of claim 20 additionally comprising a piercing member for forming the opening in the wall of the native blood vessel.

22. The system of claim 10 wherein said second connector member includes securement means for securing the bypass graft to it.

23. A system for creating a fluid communication port in an opening in the wall of a vessel, duct or lumen within the body of a living being, the opening in wall of the vessel, duct or lumen having percutaneous puncture tract contiguous therewith and extending through tissue overlying the vessel, duct or lumen, said system comprising a first connector assembly for connection to the vessel, duct or lumen at the location of the opening to form said port, said first connector assembly comprising an anchor member and a first connector member, said first connector member and said anchor member being movably coupled together and arranged so that at least a portion of each is introduced through the opening in the wall of the vessel, duct or lumen into the interior thereof, said at least one portion of said anchor member being arranged to be moved within the interior of the vessel, duct or lumen into engagement with the wall thereof adjacent the opening, said at least one portion of said first connector being arranged to be moved within the interior of the vessel, duct or lumen with respect to said anchor member, said first connector member having a free end portion having a passageway therein and arranged to be extended out of the opening in the vessel, duct or lumen while said at least one portion of said first connector is within the interior of the vessel, duct or lumen, whereupon fluid communication is established with the interior of the vessel, duct or lumen through said passageway in said first connector member.

24. The system of claim 23 additionally comprising a positioning member for moving said at least one portion of said anchor member and said at least one portion of said first connector member within the interior of the vessel, duct or lumen.

25. The system of claim 23 wherein said anchor member comprises an elongated member and having a connector-receiving opening arranged to receive a portion of said first connector member when said anchor member and said first connector member are moved with respect to each other.

26. The system of claim 24 wherein said first connector member comprises a tube having a lumen therein.

27. The system of claim 26 wherein said tube has a pair of ends, one of said ends having a flange and the other of said ends forming said free end of said first connector member, said tube being arranged to be drawn into said opening area of said anchor member, whereupon a portion of said flange abuts a portion of said anchor member.

28. The system of claim 23 additionally comprising a second connector member which is arranged to be connected to said free end of said first connector member.

29. The system of claim 28 wherein said second connector member comprises a tube and an abutment portion arranged to be disposed closely adjacent the outside of the native blood vessel contiguous with the opening therein when said first and second connector members are secured together.

30. The system of claim 29 wherein each of said first and second connector members includes means for enabling them to be snap fit together.

31. The system of claim 23 wherein said first connector assembly comprises at least one resorbable portion.

32. The system of claim 23 additionally comprising a deployment instrument for delivering said at least one portion of said anchor member and said at least one portion of said first connector member through the opening in the wall of the vessel, duct or lumen.

33. The system of claim 32 wherein said deployment instrument comprises a carrier tube having a lumen in which said anchor member and said first connector member are disposed.

34. The system of claim 33 additionally comprising a piercing member for forming the opening in the wall of the vessel, duct or lumen.

* * * * *

UNITED STATES PATENT AND TRADEMARK OFFICE
CERTIFICATE OF CORRECTION

PATENT NO.   : 6,350,280 B1                                                            Page 1 of 1
DATED        : February 26, 2002
INVENTOR(S)  : John E. Nash, Douglas G. Evans and David M. Hoganson It is certified that error appears in the above-identified patent and that said Letters Patent is hereby corrected as shown below:

Column 15,
Line 55, after the word "method" please insert the word --of--
Line 55, after the word "portion" please insert the words -- of a --
Line 56, after the word "living" please insert the word -- being --

Column 16,
Line 59, after the word "portion" please insert the words -- of a --

Column 17,
Line 13, after the word "interior" please insert the word -- of --
Line 65, after the word "in" please insert the word -- the --

Signed and Sealed this

Twenty-second Day of October, 2002

Attest:

JAMES E. ROGAN
Attesting Officer                    Director of the United States Patent and Trademark Office